US005660860A

United States Patent [19]
Fielden

[11] Patent Number: 5,660,860
[45] Date of Patent: *Aug. 26, 1997

[54] WATER-DISPERSIBLE TABLETS

[75] Inventor: Krystyna Elzbieta Fielden, Dartford, England

[73] Assignee: Glaxo Wellcome Inc., Research Triangle Park, N.C.

[*] Notice: The portion of the term of this patent subsequent to Jul. 29, 2013, has been disclaimed.

[21] Appl. No.: 317,300

[22] Filed: Oct. 3, 1994

Related U.S. Application Data

[63] Continuation of Ser. No. 181,393, Jan. 13, 1994, abandoned, which is a continuation of Ser. No. 41,126, Mar. 30, 1993, abandoned, which is a continuation of Ser. No. 827,655, Jan. 29, 1992, abandoned.

Foreign Application Priority Data

| Jan. 30, 1991 | [GB] | United Kingdom | 9102019 |
| Nov. 22, 1991 | [GB] | United Kingdom | 9124803 |
| Nov. 22, 1991 | [GB] | United Kingdom | 9124807 |
| Nov. 25, 1991 | [GB] | United Kingdom | 9125005 |

[51] Int. Cl.$^6$ .................................. A61K 9/20
[52] U.S. Cl. ............... 424/464; 424/465; 424/468; 424/469; 424/484; 514/770; 514/934; 514/965
[58] Field of Search ............... 424/464, 484, 424/465, 468, 469; 514/770, 934, 965

[56] References Cited

U.S. PATENT DOCUMENTS

| 3,427,379 | 2/1969 | Barry et al. | 424/14 |
| 3,432,593 | 3/1969 | Shepard | 424/20 |
| 3,567,819 | 3/1971 | Leonia et al. | 424/16 |
| 4,072,535 | 2/1978 | Short et al. | 106/210 |
| 4,086,335 | 4/1978 | Bruscata et al. | 514/161 |
| 4,159,345 | 6/1979 | Takeo et al. | 514/781 |
| 4,209,513 | 6/1980 | Toroda | 514/158 |
| 4,251,513 | 2/1981 | Moore et al. | 514/54 |
| 4,304,773 | 12/1981 | Wong et al. | 514/223 |
| 4,305,502 | 12/1981 | Gregory et al. | 206/532 |
| 4,322,449 | 3/1982 | Vosds et al. | 427/214 |
| 4,369,308 | 1/1983 | Trubiano | 536/106 |
| 4,371,516 | 2/1983 | Gregory et al. | 424/485 |
| 4,414,198 | 11/1983 | Michaelson | 424/44 |
| 4,517,179 | 5/1985 | Raghunathan | 514/249 |
| 4,600,579 | 7/1986 | Salpekar et al. | 424/80 |
| 4,602,017 | 7/1986 | Sawyer et al. | 514/242 |
| 4,631,305 | 12/1986 | Guyer et al. | 523/400 |
| 4,661,521 | 4/1987 | Salpekar et al. | 514/613 |
| 4,711,777 | 12/1987 | Tan et al. | 424/79 |
| 4,757,090 | 7/1988 | Salpekar et al. | 514/613 |
| 4,774,083 | 9/1988 | Tan et al. | 424/79 |
| 4,781,925 | 11/1988 | Michelucci et al. | 424/465 |
| 4,832,956 | 5/1989 | Gergely et al. | 424/466 |
| 4,837,031 | 6/1989 | Denton et al. | 424/464 |
| 4,847,249 | 7/1989 | Sawyer et al. | 514/242 |
| 4,904,477 | 2/1990 | Ho et al. | 424/465 |
| 4,910,023 | 3/1990 | Botzolakis et al. | 423/470 |
| 4,925,676 | 5/1990 | Selassie et al. | 424/470 |
| 4,927,639 | 5/1990 | Selassi et al. | 424/497 |
| 4,950,484 | 8/1990 | Olthoff et al. | 424/464 |
| 4,965,072 | 10/1990 | Alexander et al. | 424/458 |
| 4,968,517 | 11/1990 | Gergely et al. | 426/285 |
| 4,970,078 | 11/1990 | Holinej | 424/465 |
| 4,999,200 | 3/1991 | Casilian | 424/480 |
| 5,006,345 | 4/1991 | Lang | 424/467 |
| 5,037,658 | 8/1991 | Urban et al. | 424/469 |
| 5,047,247 | 9/1991 | Milovac et al. | 424/465 |
| 5,049,586 | 9/1991 | Ortega et al. | 514/557 |
| 5,064,656 | 11/1991 | Gergely et al. | 424/463 |
| 5,069,910 | 12/1991 | Kovacic et al. | 424/464 |
| 5,073,377 | 12/1991 | Alexander et al. | 424/494 |
| 5,085,869 | 2/1992 | Olthoff et al. | 424/499 |
| 5,087,454 | 2/1992 | Duerholz et al. | 424/464 |
| 5,136,080 | 8/1992 | Miller et al. | 585/410 |

FOREIGN PATENT DOCUMENTS

| 89096/91 | 6/1992 | Australia . |
| 2013918 | 10/1990 | Canada . |
| 0 261 595 | 3/1988 | European Pat. Off. . |
| 0 294 933 | 5/1988 | European Pat. Off. . |
| 0 305 843 | 3/1989 | European Pat. Off. . |
| 0 350 701 | 1/1990 | European Pat. Off. . |
| 0 391 851 | 3/1990 | European Pat. Off. . |
| 0 372 934 | 6/1990 | European Pat. Off. . |
| 0 391 851 | 10/1990 | European Pat. Off. . |
| 247892 | 4/1991 | European Pat. Off. . |
| 0 459 819 | 12/1991 | European Pat. Off. . |
| 0 459 830 | 12/1991 | European Pat. Off. . |
| 0 265 226 | 5/1992 | European Pat. Off. . |
| 2016622 | 10/1971 | Germany . |
| 24078 | 10/1968 | Japan . |
| 54-129129 | 10/1979 | Japan . |
| 56-127309 | 10/1981 | Japan . |
| 57-11911 | 1/1982 | Japan . |

(List continued on next page.)

OTHER PUBLICATIONS

Rudnic et al, Drug Development and Industrial Pharmacy 7(3), pp. 347–358 (1981).
Patel, N.K., Kennon L and Levinson S.R., Pharmaceutical Suspensions, Chapter 16 from the Theory and Practice of Industrial Pharmacy (ed Lachman, Lieberman and Kanig), 1986.
Lowenthal J. Pharm Sci, vol. 61: No. 11, pp. 1695–1711 (1972).
Holstius et al; J. Amer. Pharm. Sci 41,505 (1952).
Patel et al, Indian J. Pharm. 26,313 (1964).
Patel et al. Indian J. Pharm. 28,244 (1966).
Smeczi et al. Acta Pharm. Hungary, 40, 124 (1970).
Bilups et al, Amer J. Pharm. 136,25 (1964).

(List continued on next page.)

Primary Examiner—Raj Bawa
Attorney, Agent, or Firm—Nixon & Vanderhye

[57] ABSTRACT

A water-dispersible tablet comprises acyclovir and a dispersing agent. The dispersing agent is a swellable clay such as a smectite, e.g. Veegum F or bentonite, and is generally present within the granules of the tablet to provide a tablet which is capable of dispersing in water within 3 minutes to provide a dispersion which will pass through a 710 μm sieve. The tablet can be optionally film-coated in which case the dispersion time is less than 5 minutes.

21 Claims, No Drawings

FOREIGN PATENT DOCUMENTS

| | | |
|---|---|---|
| 57-11913 | 1/1982 | Japan. |
| 64-42347 | 2/1982 | Japan. |
| 57-56434 | 11/1983 | Japan. |
| 58-194816 | 11/1983 | Japan. |
| 62-227729 | 10/1987 | Japan. |
| 1-93541 | 4/1989 | Japan. |
| 2-111620 | 4/1990 | Japan. |
| 2-145501 | 6/1990 | Japan. |
| 2-290801 | 11/1990 | Japan. |
| 3-264502 | 11/1991 | Japan. |
| 207678 | 11/1986 | New Zealand. |
| 222701 | 6/1990 | New Zealand. |
| 777516 | 6/1957 | United Kingdom. |
| 837451 | 6/1960 | United Kingdom. |
| 1 317 400 | 5/1973 | United Kingdom. |
| 1 421 964 | 1/1976 | United Kingdom. |
| 1 480 175 | 7/1977 | United Kingdom. |
| 1 480 188 | 7/1977 | United Kingdom. |
| 1533243 | 11/1978 | United Kingdom. |
| 1546448 | 5/1979 | United Kingdom. |
| 1548022 | 7/1979 | United Kingdom. |
| 2033225 | 5/1980 | United Kingdom. |
| 1601833 | 11/1981 | United Kingdom. |
| 2086725 | 5/1982 | United Kingdom. |
| 2119355 | 11/1983 | United Kingdom. |
| 2124078 | 2/1984 | United Kingdom. |
| 2157170 | 10/1985 | United Kingdom. |
| 1 443 023 | 7/1986 | United Kingdom. |
| 2197197 | 5/1988 | United Kingdom. |
| 2 249 957 | 5/1992 | United Kingdom. |
| 2 249 957A | 5/1992 | United Kingdom. |
| 83/00809 | 3/1983 | WIPO. |
| 87/05804 | 10/1987 | WIPO. |
| 91/03241 | 3/1991 | WIPO. |
| 91/07174 | 5/1991 | WIPO. |

OTHER PUBLICATIONS

Patel et al. Indian J. Pharm., 25,220 (1963).
Birmancevic et al. Arh. Farm. 31 (1–2),45–54 (1981).
Birmancevic et al. Acta, Pharmaceutica Yugoslavia 237–240 (1974).
Birmancevic et al. (Arch. Farm. 28, 21–28 (1978).
Borzonuv et al. Chem Abstr., 69 1097q (1968).
Borzonuv et al. Chem Abst., 71 3385y (1969).
Selmeczi et al. Chem Abst 70, 14395q (1969).
Saufiulin et al. Chem Abst 58, 13727a (1963).
Kuever et al. J. American Pharm. Ass. Sci, 17, 365 (1928).
Shotton et al J. Pharm Pharmac., 24, 798–803 (1972).
Shotton et al J. Pharm. Sci., 65 1170–1174 (1976).
Pennwalt Corp; Raghunathan, Y, pp. 1–33; 27678; Cellulose and Starch (1984).
Faracia Polska; No. 7, pp. 505–509 (1966).
Britain Pharmacopeia vol. 11, pp. 891–895 (1988).
R. F. Shangraw; University of Maryland; "Specialty Tablets and Capsules" pp. 427–440–(1990).
Veegum – The Supernatural Ingredient: R. T. Vanderbilt & Co., Booklet (1987).
Pharmasorb: Lawrence Industries, pp. 1–10 (1986).
Wal et al "Applications of the Montmorillonites in Tablet Making" J. Pharm. Sci., 55: 1244–1248 (1966).
Wai & Banker "Some Physicochemical Properties of the Montmorillonites" J. Pharm. Sci., 55, 1215–1220 (1966).
Granberg et al "The use of Dried Bentonite as a Disintegrating Agent in Compressed Tablets of Thyroid" J. Am. Pharm. Asoc. Sci., 43: 648–7651 (1949).
Gross et al "A Comparative Study of Tablet disintegrating Agents": J. Am. Pharm. Assoc. Sci., 41: 157–161 (1952).
Firouzabadian et al "Some recently Developed Chemicals as Disintegrating Agents for Compressed Tablets": J. Am. Pharm. Assoc. Sci., 43 248–250 (1954).
Ward et al "Evaluation of Tablet Disintegrants" Drug Cosmetic Ind. 91: 35–36, 92, 110–111 (1962).
Nair et al "Studies on Disintegration of Compressed Tablets I. Effect on Disintegration of the Procedure Used in Incorporating the Disintegrating Agent": J. Am Pharm. Assoc. Sci., 46: 131–134 (1957).
Patel et al "Veegum as Binding Agent for Compressed Tablets" Indian J. Pharm., 19: 4–10 (1957).
Feinstein et al "Comparative Study of Selected Disintegrating Agents": J. Pharm. Sci. 55: 332–334 (1966).
Varley, A, "The generic Inequivalence of Drugs" JAMA, 206: 1745–1748 (1968).
Delonca et al "Study of the Activity of Some Disintegrants as a Function of Procedure and of the Solubility of the Active Principles" J. Pharm. Belg. 26(4): 447–458 (1971).
Wagner et al "In vivo and In vitro availability of Commercial Warfarin Tablets" J. Pharm. Sci. 60:666–677 (1971).
McGinty et al "Optimization of Slow–Release Tablet Formulations Containing Montmorillonite I. Properties of Tablets" Drug Development and Industrial Pharmacy 6: 399–410 (1980).
Bargava et al "An Evaluation of Smecta as a Tablet Disintegrant and Dissolution Aid" Drug Development and Industrial Pharmacy 17: 2093–2102 (1991).
Barr, M. "In Pharmaceutical Systems . . . Clays as Dispersion Stabilizers" J. Amer. Pharm. Assoc. Sci. Ed. 46: 486–493 (1957).
U.S. Pharmacopoeia, pp. 579, 1573, 1574, 1534 and 1535 (1985).
British Pharmacopoeia, pp. 27, 28, 51, 52, 62, 323–325 (1985).
Martindale, The Extra Pharmacopoeia, 29th Edition, 1077, 1092 and 1433 (1989).
Armstrong, N. "Tableting" from Pharmaceutics: The Science of Dosage Form Design (Ed. Aulton): 647–668 (1988).
Rubinstein, M. "Tablets" from Pharmaceutics The Science of Dosage Form Design, (Ed. Aulton): 304–321 (1988).
Rudnic et al "Oral Solid Dosage Forms" from Remington's Pharmaceutical Sciences (Ed. Gennaro) pp. 1633–1665 (1990).
Disento, A. "Bioavailability and Bioequivalency Testing" from Remington's Pharmaceutical Sciences (ed. Gennaro), pp. 1451–1458 (1990).
Marshall et al "Tablet Dosage Forms" from Modern Pharmaceutics (eds. Banker G & Rhodes C) pp. 355–425 (1990).
Shangraw R. "Specialty Tablet and Capsules" from Modern Pharmaceutics (eds. Banker, G & Rhodes, C) pp. 427–440 (1990).

WATER-DISPERSIBLE TABLETS

This is continuation of application(s) Ser. No. 08/181,393 filed on Jan. 13, 1994, abandoned which is a continuation of Ser. No. 08/041,126, filed on Aug. 30, 1993, abandoned which is a continuation of Ser. No. 07/827,655, filed on Jan. 29, 1992, abandoned.

The present invention relates to a water-dispersible tablet formulation containing acyclovir.

BACKGROUND OF THE INVENTION

Acyclovir (UK Patent Specification No. 1523865; U.S. Pat. No. 4,199,574) is a compound which has been found to have potent activity against viruses of the herpes family, particularly herpes simplex and herpes varicella zoster. Such activity has been demonstrated by the outstanding success of acyclovir in the therapeutic treatment of clinical conditions such as genital herpes caused by the herpes simplex virus, or chicken pox or shingles, caused by the varicella zoster virus.

In the treatment of certain conditions, it may be necessary to administer acyclovir to the patient in relatively large dosages to achieve the effective therapeutic levels of drug in the plasma, particularly when oral administration is desired. For example, in the treatment of shingles, it is recommended to administer acyclovir at a dosage regime of 800 mg five times per day. A tablet formulation containing 800 mg of acyclovir is currently available but its relatively large size sometimes renders it difficult to swallow by elderly patients, such patients being particularly susceptible to shingles.

Known water-dispersible tablets include effervescent formulations which rely on the formation of a gas to quickly break up the tablet, but these involve expensive methods of manufacture and strict regulations for such manufacture. Other known water-dispersible tablets use disintegrating agents such as microcrystalline cellulose used in Feldene R dispersible tablets. We have tested well-known disintegrating agents (incorporated both internally and externally to the preformed granules) such as sodium starch glycollate (e.g. Explotab), cross-linked povidone (e.g. Kollidon CL) and a cross-linked sodium carboxymethylcellulose (e.g. Starch, Avicel PH102, and Ac-Di-Sol) in an acyclovir tablet, but found that they did not provide a satisfactory water-dispersible formulation. We furthermore tested on ion exchange resin (Amberlite 1RP88) as a disintegrating agent and incorporated surface active agents (e.g. sodium lauryl sulphate and sodium docusate) in an attempt to improve tablet wetting and penetrating of water during dispersion, but in all cases the disintegration time was high.

SUMMARY OF THE INVENTION

After considerable research and investigation, we have now suprisingly found that the use of a swellable clay within the granulate of an acyclovir tablet formulation provides a tablet which has good dispersibility in water to provide a dispersion which can be drunk by a patient.

Swellable clays such as Veegum$^R$ and other magnesium aluminum silicates have previously been studied and proposed for use as disintegrating agents, binders and lubricants in the manufacture of tablets, but such studies and proposals were exclusively with respect to tablets intended for swallowing and not for water-dispersible tablets (Rubenstein, Pharmaceutics—The Science of Dosage Form Design (1990) for disintegrants see p 312 and 314). Moreover, there has never been any suggestion that a clay would be suitable to meet the more stringent requirements for dispersible tablets. Tablets for swallowing need only have a disintegration time in water of less 15 minutes and be able to form particles on disintegration in water that can pass through a 2.00 mm mesh aperture (British Pharmacopia test for swallowable tablets). Such long disintegration times and large particle sizes are entirely unsuitable for a dispersible tablet.

Even when swellable clays have been proposed as disintegrating agents for swallowable tablets, they are not regarded as very suitable for such use because their off-white appearance can often discolour the tablet and because they are not as effective as other disintegrating agents (Banker and Anderson—Theory and Practice of Industrial Pharmacy p 328 (1986) and Bhargava et al—Drug Development and Industrial Pharmacy, 17(15), 2093–2102(1991). In fact, bentonite is identified in Marshall and Rudnic, Modern Pharmaceutics (1990) p 374, as the least swellable of the ten disintegrants listed. There is no mention in the above textbook references of how the swellable clay should be incorporated—i.e. by intra-granular addition or by extra-granular addition. In the former case, the clay would be included in the mixture from which the granulate is formed; in the latter case the clay would be added to the per-formed granulate.

In J. Pharm. Sci, 55, 1244 (1966), Wei et al. reviewed the following papers relating to swellable clays such as Veegum and bentonite as disintegrating agents; Wai et al., J. Pharm. Sci., 55, 1215(1966); Granberg et al., J.Am.Pharm.Assoc.Sci, 38, 648(1949); Gross et al., J.Am.Pharm.Assoc.Sci, 41, 157(1952); Firouzabadian et al., J.Am.Pharm.Assoc.Sci, 43, 248(1954); Ward et al., Drug Cosmetic Ind, 91, 35(1962); Nair et al., J.Am.Pharm.Assoc.Sci, 46, 131(1957); and Patel et al., Indian J.Pharm., 19, Jan. 1957. Wai et al., then compared three grades of Veegum evaluating both extra-granular and intra-granular addition and concluded that "the clays were not good disintegrating agents when wet granulated" (i.e. intra-granular addition), and then went on to recommend extra-granular addition. Furthermore R. T. Vanderbilt and Co. (Manufacturers of Veegum) in their publication "Veegum—The Versatile Ingredient for Pharmaceutical Formulations" at p 19 describe a tablet formulation in which Veegum is added after granulation (tablet No. 2). There is no reference in the publication to a formulation of a tablet in which Veegum is added during granulation.

In contrast to the above recommendations, we have found that a swellable clay such as Veegum must be added during granulation to meet the British Pharmacopoeia (B.P.) standard for dispersible tablets (presently set at a dispersion time of 3 minutes or less). If the swellable clay is added only after granulation the dispersion time is too high to meet the above standard.

By using Veegum and other swellable clays in the manner described above, we have been able to prepare water-dispersible tablets containing acyclovir which can be readily be dispersed in water to form a dispersion which can be drunk by a patient.

According to the present invention there is provided a water-dispersible tablet comprising acyclovir, together with an effective amount of a pharmaceutically acceptable swellable clay to provide a tablet which is capable of dispersing in water within a period of 3 minutes to provide a dispersion which is capable of passing through a sieve screen with a mesh aperture of 710 μm in accordance with the test for dispersible tablets defined in the British Pharmacopoeia, 1988, Volume II, page 895 which disclosure is herein incorporated by reference.

The above-mentioned test for dispersion time is carried out using the following apparatus and method:

Apparatus (a) A rigid basket-rack assembly supporting six cylindrical glass tubes 75.0 to 80.0 mm long, 21.5 mm in internal diameter and with a well thickness of about 2 mm.

(b) A cylindrical disc for each tube, each 20.55 to 20.85 mm is diameter and 9.35 to 9.65 mm thick, made of transparent plastic with a relative density of 1.18 to 1.20, pierced with five holes, each 2 mm in diameter, one in the centre and the other four spaced equally on a circle of radius 6 mm from the centre of the disc. Four equally spaced grooves are cut in the lateral surface of the disc in such a way that at the upper surface of the disc they are 9.5 mm wide and 2.55 mm deep and at the lower surface 1.6 mm square.

(c) The tubes are held vertically by two superimposed transparent plastic plates 90 mm in diameter and 6 mm thick, perforated by six holes having the same diameter as the tubes. The holes are equidistant from the centre of the plate and are equally spaced from one another. Attached to the underside of the lower plate is a piece of woven gauze made from stainless steel wire 0.635 mm in diameter and having nominal mesh apertures of 2.00 mm.

(d) The plates are held rigidly in position and 77.5 mm apart by vertical metal rods at the periphery and a metal rod is also fixed to the centre of the upper plate to enable the assembly to be attached to a mechanical device capable of raising and lowering it smoothly through a distance of 50 to 60 mm at a constant frequency of between 28 and 32 cycles per minute.

(e) The assembly is suspended in the liquid medium in a suitable vessel, preferably a 1000-ml beaker. The volume of liquid is such that when the assembly is in the highest position the wire mesh is at least 15 mm below the surface of the liquid and when the assembly is in the lowest position the wire mesh is at least 25 mm above the bottom of the beaker and the upper open ends of the tubes remain above the surface of the liquid.

(f) A suitable device maintains the temperature of the liquid at 19° C. to 21° C.

The design of the basket-rack assembly may be varied provided that the specifications for the glass tubes and wire mesh are maintained.

Method

Introduce one tablet into each tube, optionally adding a disc to each tube. Suspend and assembly in the beaker containing the specified liquid and operate the apparatus for a maximum period of three minutes. Remove the assembly from the liquid. The tablets pass the test if all six have dispersed within a period of three minutes.

The above-mentioned test for dispersion quality (i.e. uniformity of dispersion) is carried out as follows:

Place two tablets in 100 ml of water and stir until completely dispersed. A smooth dispersion is produced which passes through a sieve screen with a nominal mesh aperture of 710 μm.

The present invention further provides a process for the preparation of a water-dispersible tablet comprising acyclovir, together with an effective amount of a pharmaceutically acceptable swellable clay which comprises bringing acyclovir into association with the said swellable clay to provide a water-dispersible tablet which is capable of dispersing in water within a period of 3 minutes to provide a dispersion which is capable of passing through a sieve screen with a mesh aperture of 710 μm in accordance with the test for dispersible tablets defined in the British Pharmacopoeia, 1988, Volume II, page 895.

Preferably said process comprises the steps of:

a) admixing in dry, finely-divided form acyclovir with an effective amount of a pharmaceutically acceptable swellable clay, optionally with the addition of one or more other pharmaceutical carriers or excipients;

b) addition of a quantity of a pharmaceutically acceptable liquid sufficient to moisten the dry mixture;

c) granulation of the resulting moist mixture to form granules;

d) drying the granules and optionally blending the granules with other optional carriers or excipients such as lubricants, glidants, flavouring agents and disintegrating agents; and e) compression of the granules to form a tablet which is capable of dispersing in water within a period of 3 minutes to provide a dispersion which is capable of passing through a sieve screen with a mesh aperture of 710 μm in accordance with the above defined British Pharmacopoeia test for dispersible tablets.

A tablet according to the invention, as well as being quickly dispersible in water, has the added advantage that it meets the British Pharmacopoeia (B.P.) test for dispersible tablets in respect of dispersion times and dispersion quality (i.e. passage through a 710 μm sieve).

Preferably the dispersion time of a tablet according to the invention is less than 2 minutes, more preferably less than 1.50 minutes and most preferably less than 1 minute.

A further advantage of the tablets according to invention is that because a relatively fine dispersion is formed the tablet will have a lower dissolution time and thus the drug may be absorbed into the blood stream much faster. Furthermore the fast dispersion times and relatively fine dispersions obtained with tablets according to the invention are also advantageous for swallowable tablets. Thus tablets according to the invention can be presented both for dispersion in water and also for directly swallowing. Those tablets according to the invention that are intended for swelling are preferably film-coated to aid swallowing. Such film-coating however increases the dispersion time up to 5 minutes determined in accordance with the above-mentioned B.P. test.

According to a further feature of the present invention therefore we provide a water-dispersible film-coated tablet comprising acyclovir together with an effective amount of a pharmaceutically acceptable swellable clay to provide a film-coated tablet which is capable of dispersion in water within a period of 5 minutes to provide a dispersion which is capable of passing through a sieve screen with a mesh aperture of 710 μm in accordance with the above-defined British Pharmacopoeia test for dispersible tablets subject to the variation of the said period specified in the test from 3 minutes to 5 minutes. The references herein to tablets according to the invention include both film-coated and non-film-coated tablets.

After the dispersion has passed through the 710 μm mesh screen, there should be substantially no residue, except fragments of undissolved tablet coating or shell, remaining on the screen or adhering to the lower surface of the disc, if a disc optionally has been used; and if any residue remains, it should consist of a soft mass having no palpably firm, unmoistened core.

The particle size distribution of the dispersion is set out in the following table with the increasingly preferred values being quoted from left to right.

| Particle Size (μm)* | BP Standard | Preferably | More Preferably | Most Preferably |
|---|---|---|---|---|
| <710 | <100% | 100% | 100% | 100% |
| <300 | — | >50% | >70% | >80% |
| <200 | — | — | >50% | >70% |
| <150 | — | — | — | >50% |

*(equivalent spherical volume diameter)

The term "swellable clay" as used herein includes layered clays (such as smectites), porous fibrous clay minerals, and synthetic clay materials related in structure to layered clays and porous fibrous clays.

the term "layered clays" as used herein includes substantially homogeneous layered clays and mixtures thereof, and interstratified or mixed layered clays. Substantially homogeneous layered clays includes the smectite groups for example dioctahedral and trioctahedral types. Examples of dioctahedral smectites are the montmorillonite group (montmorillonoids); magnesium and other (e.g. calcium) aluminum silicates such as Veegum in its various grades e.g. Veegum, Veegum HV, Veegum F, and Veegum WG); almasilate; fullers earth (e.g. Surry finest); American fullers earth; bentonite; beidellite; cheto montmorillonite, Wyoming montmorillonite, Utah montmorillonite; Tatalia and Chambers montmorillonites; and iron rich smectites such as nontrite (e.g. Garfield nontronite) and ferrian smectites.

Examples of triccatahedral smectites (also known as saponites) are Swinefordite, hectorite, stevensite. Examples of smectites containing more unusual elements are Volkhonite, Medmontite, Sauconite, nickel smectites and vanadium smectites. As well as the montmorillonite group, related smectites such as vermiculites may also have application.

The term "interstratified or mixed layer clays", as used herein includes clays involving different layers arranged in a regular or irregular structure. The most common examples of such clays have generally two components in substantially equal proportions and have been given mineral names such as rectorite (mica-smectite), hydrobiotite (biotite-vermiculite), corrensiten (chlorite-smectite) allettite (talc-saponite). More irregular arrangements include illite-smectite, chlorite-smectite, and kaolinite-smectite. Further examples of interstratified clays are tosudite, tarasovite, allevardite, Japanese bentonite ("acid clays"), AWAZU acid clay, and kaolinite-smectite. Other mixed layer clays may include one or more of the following minerals; clinchlore, chamosite, nimite, thuringite, sudoite, and cookeite. Mixed layer smectities are also known e.g. interdispersed montmorillonite and beidellite layers. The layers of mixed layer clays are be homogeneous or non-homogeneous.

The term "porous fibrous clays" includes palygorskite and sepiolite such as, for example attapulgite and American fuller's earth.

The term "synthetic clay materials" as used herein includes materials related in structure to layered clays and porous fibrous clays such as synthetic hectorite (lithium magnesium sodium silicate) for example lapnite$^R$.

It will be appreciated that within the scope of the invention the following classes of clays have application alone or in combination and in mixed layer clays; kaolinites, serpentines, pyrophyllites, talc, micas and brittle micas, chlorites, smectites and vermiculites, palygorskites and sepiolites. Other phyllosilicates (clay minerals) which may be employed in the tablets according to the invention are allophane and imogolite.

The following references describe the characterisation of clays of the above types: Chemistry of Clay and Clay Minerals. Edited by A.C.D. Newman. Mineralogical Society Monograph No. 6, 1987, Chapter 1; S. W. Bailey; Summary of recommendations of AIPEA Nomenclature Committee, Clay Minerals 15, 85–93; and A Handbook of Determinative Methods in Mineralogy, 1987, Chapter 1 by P. L. Hall.

Suitably the swellable clay is a pharmaceutically acceptable crystalline mineral clay having a lattice structure which expands upon hydration, preferably a pharmaceutically acceptable smectite or attapulgite clay, especially a montmorillonoid, more preferably yet a montmorillonoid chosen from the group consisting of montmorillonite, sauconite, vermiculite, bentonite and hectorite, still more preferably an aluminum magnesium silicate and most preferably Veegum$^R$.

The term "smectite" as used herein in relation to tablets of the present invention includes the smectites as exemplified herein and with reference to O'Brian P. and Williamson C. J., in "Clays and Clay Minerals vol. 38 No. 3 pp 322–326, 1990" and the other clay nomenclature references set out hereinbefore.

The term "magnesium aluminium silicate" as used herein in relation to tablets of the present invention should be understood to include the Aluminium Magnesium Silicate defined in the *British Pharmacopoeia*, volume 1, pages 27–28, 1988 and the Magnesium Aluminium Silicate defined in the *United States Pharmacopoeia, National Formulary XVI*, pages 1943–1944, 1990. Advantageously, said silicate is in the form of a microfine powder having a No. 325 US Standard mesh particle size, a viscosity of 250 cps (±25%) for a 5.5% (w/v) aqueous dispersion and an acid demand (the volume in ml. of 0.1N hydrochloric acid required to reduce the pH of one gram to 4) of 6–8: such a material is available as VEEGUM F (R. T. Vanderbilt Co., New York, N.Y., U.S.A.; K & K-Greeff Chemicals Ltd., Croydon, Surrey CR9 3QL, England).

The amount of swellable clay employed in the tablet according to the invention generally depends on the weight of the tablet. Experiments with acyclovir indicate for a 100 mg tablet, amounts as low as 0.25% w/w of tablet can be used whereas for tablets of about 1000 mg to 1200 mg up to 60% w/w, advantageously up to 50% w/v preferably up to 40% w/w could be used to give a satisfactory dispersible tablet in accordance with the invention. Other practical considerations such as poor flow and compression properties may, however, limit the maximum percentage weight of clay which can be incorporated within any given weight of tablet. In our experiments up to 40% w/w of swellable clay was used for a tablet having a total weight of 1100 mg and gave fine dispersions and fast dispersion times.

Thus for a dispersible tablet according to the present invention, the intra-granular amount of swellable clay such as a crystalline mineral clay for example, magnesium aluminum silicate is suitably present in the following general ranges 0.25 to 60% w/w, preferably 0.25 to 50% w/w, more preferably 0.5 to 50% w/w, more preferably still 1 to 50% w/w, more preferably still 1 to 40% w/w, more preferably still 2 to 20% w/w, more preferably still 2.5 to 20% w/w, still more preferably 3 to 10% w/w, and most preferably 5 to 10%, most desirably about 5% w/w.

The tablets according to the invention will generally contain a predetermined amount of acyclovir depending on the desired dosage and the total weight of the tablet.

The tablets generally contain 100 to 1000 mg, preferably 200 to 800 mg, such as 400 to 800 mg of acyclovir. Such dosage units may be administered one or more times, for example up to five times, per day, at the discretion of the physician, according to the age and condition of the patient and the particular condition being treated. For an acyclovir tablet having a total weight about 1000 to 1200 mg and containing about 750 to 850 mg of acyclovir, the swellable clay e.g. Veegum F, is preferably present in an amount of 40 to 120 mg intragranularly.

In general the tablets according to the invention contain 20 to 90% w/w, preferably 45 to 85% w/w of acyclovir.

When acyclovir is present in an amount of at least 60% w/w in tablets according to the invention, we have suprisingly found that the dispersion time remains substantially constant over a range of tablet hardnesses. This is a considerable quality control advantage since in industrial manufacture it is essential to maintain a constant tablet hardness. Tablets according to the invention can thus be produced with sufficient hardness and friability so that they can easily be film-coated. A tablet according to the invention should desirably have a friability of about 2% or less, preferably 0.5% or less.

Based on experiments that we have carried out, it has been found that is addition to the amount of swellable clay present within the granules of the tablet, a further amount of swellable clay may be present outside the granules. At very low intra-granular amounts (such as 1% w/w or below), higher extra-granular amounts (such as about 10% w/w or more) may decrease the dispersion time, but in general extra-granular addition has little or no effect on the dispersion time. The maximum percentage(s) of the clay present within the granules and, optionally outside the granules, may be limited by other practical considerations such as poor flow and compression properties.

Other excipients suitable for inclusion in the tablets according to the invention include the following:

a) Binders and Adhesives: we have found with some acyclovir tablet formulations that if there is sufficient amount of swellable clay such as Veegum F present within the granules, then a separate binder is not required (i.e. the clay also acts as a binder). Preferably however a separate binder is present in a sufficient amount to provide a tablet having a satisfactory tablet hardness and satisfactory dispersion characterstics. The amount of binder will vary depending on the overall tablet formulation and type of binder used but general functional limits for most tablets of the invention are 0 to 25% w/w. The following binders and amounts are suitable for inclusion in a tablet according to the invention. The concentration of the binder in the granulation fluid (% w/w) is given (% w/w in tablet will vary according to the volume of granulating solution used to form a satisfactory tablet): Examples of binders are: acacia mucilage 0 to 25% w/v, preferably 1 to 5% w/v, alginic acid 0 to 20.0% w/v, preferably 1 to 5% w/v, polyvinylpyrrolidone (povidone) 0 to 15.0% w/v, preferably 0.5 to 5% w/v, gelatin 0 to 20.0% w/v, preferably 1 to 5.0% w/v, sucrose 0 to 70.0% w/v, preferably 2.0 to 20.0% w/v, starch mucilage 0 to 10.0% w/v, preferably 0.5 to 5.0% w/v, pregelatinised starch 0 to 10.0% w/v, preferably 0.5 to 5.0% w/v, starch paste 0 to 10.0% w/v, preferably 5.0 to 10.0% w/v, sodium alignate 0 to 5.0% w/v, preferably 1.0 to 3.0% w/v, sorbitol 0 to 10.0% w/v, preferably 3.0 to 10.0%w/v, tragacanth 0 to 20% w/v, preferably 5.0 to 10.0% w/v, glucose 0 to 50%, preferably 5 to 25% w/v, hydroxypropylmethyl cellulose (HPMC) 0 to 10% w/v, preferably 1.0 to 5.0% w/v, magnesium aluminum silicate 0 to 40% w/v, preferably 2 to 10% w/v, starch paste 0 to 25% w/v, preferably 5 to 15% w/v, polyvinylpyrrolidone 0 to 15% w/v, preferably 3 to 10% w/v, carboxymethylcellulose sodium 0 to 10% w/v, preferably 1 to 6% w/v, dextrin 0 to 50% w/v, preferably 5 to 25% w/v, ethyl cellulose 0 to 10% w/v, preferably 1 to 6% w/v, polyethylene glycol 0 to 5% w/v, guar gum 0 to 10% w/v, preferably 1 to 5% w/v, zein 0 to 30% w/v, preferably 1 to 10% w/v, hydroxyethyl cellulose 0 to 5% w/v, preferably 2 to 4w/v, hydroxypropyl cellulose up to 5% w/v, preferably 2 to 4% w/v, methyl cellulose up to 20% w/v, preferably 1 to 10% w/v, polymethacrylates up to 25% w/v, preferably 5 to 10% w/v, carboxymethylcellulose calcium 0 to 20% w/v, preferably 5 to 10% w/v.

b) Disintegrating agents: Tablets according to the invention can be formulated in the absence of separate disintegrating agents although their inclusion may be advantageous for their disintegration in water as an adjunct to the dispersion afforded by the clay above. Examples of suitable disintegrating agents which can optionally be incorporated into a tablet according to the invention are: microcystalline cellulose (e.g. Avicel R) 0 to 30% w/w, preferably 5 to 10% w/w, Sodium carboxymethyl cellulose (e.g. Nymcel R) 0 to 5% w/w, preferably 1 to 2% w/w, calcium carboxymethyl cellulose 0 to 20% w/w, preferably 1 to 5% w/w, modified cellulose gum (e.g. Ac-Di-Sol R) 0 to 10% w/w, preferably 1 to 5% w/w, cross-linked povidone 0 to 10% w/w, preferably 2 to 6% w/w, alginic acid and alginates 0 to 10% w/w, 2 to 5% w/w, pregelatinised starch 0 to 10% w/w, preferably 0.5 to 5% w/w, sodium starch glycollate (e.g. Explotab R, Primojel R) 0 to 10% w/w, preferably 0.5 to 5% w/w, modified corn starch (e.g. starch 1500 R) 0 to 20% w/w, preferably 1 to 10% w/w, starch (e.g. potato/maize starch) 0 to 15% w/w, preferably 0.2 to 10% w/w, ion exchange resin such as polacrin potassium (e.g. Amberlite IRP-88) up to 5% w/w, preferably 0.5 to 2.0% w/w.

Early work is supportive of the view that if LHPC is used as suitable dispersion can be obtained without the need for a separate wetting agent/surfactant.

c) Fillers: these serve the purpose of bulking up the tablet to a suitable size and aiding compressibility especially in lower dosage tablets. The amount of filler depends on its type, size of tablet and amount of active compound. When the concentration of active compound is below 60% w/w, more preferably 45% w/w and most preferably below 30% w/w, an inorganic water-insoluble filler is advantageously used. Examples of water-soluble fillers (which can be used in general quantities of 0 to 95% w/w) are: soluble lactose, compressible sugar, confectioners sugar, dextrose, mannitol, sodium chloride, sorbitol, xylitol, sodium chloride F. Examples of water-insoluble fillers (which can be used in general quantities of 0 to 93% w/w) are: calcium carbonate, magnesium carbonate, calcium phosphate (e.g. di and tri basic calcium phosphate), calcium sulphate, kaolin, microcystalline cellulose, powdered cellulose, pregelatinized starch 5 to 75%, starch, barium sulphate, magnesium trisilicate, aluminum hydroxide.

Inclusion of a filler having a negative heat of solution in water, for example mannitol, sorbitol and xylitol, provides tablets which, in addition to being water-dispersible, are especially suitable for chewing in the mouth, the dissolving of such an excipient in the saliva producing a cool, pleasant sensation.

d) Lubricants: Generally lubricants are used in as low an amount as possible. Examples of lubricants with percentage weights which are suitable for a tablet are: stearates (e.g. magnesium or calcium stearate) 0.2 to 5% w/w, preferably 0.25 to 1% w/w, talc 0.19 to 5% w/w, preferably 1 to 2% w/w, polyethylene glycol 0.19 to 5% w/w, preferably 2 to 5% w/w, liquid paraffin 0.18 to 5% w/w, preferably 2 to 5% w/w, sodium lauryl sulphate 0.19 to 5% w/w, preferably 0.5 to 2% w/w, magnesium lauryl sulphate 0.12 to 5% w/w, preferably 1 to 2% w/w, colloidal silicon dioxide 0.1 to 5% w/w, preferably 0.1 to 1.0% w/w, palmitostearate 0.01 to 5% w/w, preferably 1 to 3% w/w, stearic acid 0.01 to 5% w/w, preferably 1 to 3% w/w, zinc stearate 0.01 to 2% w/w, 0.5 to 1.5% w/w, hydrogenated vegetable oil 0.5 to 5% w/w, preferably 1 to 3% w/w. More suitably the lower value is 0.255.

e) Wetting agents/surfactants: examples with suitable amounts are: sodium dodecyl sulphate 0 to 10% w/w, preferably 0.5 to 2% w/w, sodium lauryl sulphate 0 to 10% w/w, preferably 0.1 to 3.0% w/w, polyoxyethylene sorbitan fatty acid esters (Tweens) 0 to 3% w/w, preferably 0.05 to 1.0% w/w, polyoxyethylene stearates 0 to 2% w/w, preferably 0.05 to 1.0% w/w, sorbitan fatty acid esters (Spans) 0 to 3% w/w, preferably 0.05 to 1.0% w/w.

f) Glidants: for example, talc 0 to 5% w/w, preferably 1 to 2% w/w, starch 0 to 15% w/w, preferably 2 to 10% w/w, magnesium stearate up to 5%, preferably 0–2.0% w/w, silica derivatives generally 0 to 1% w/w, preferably 0.2 to 0.5% w/w, such as colloidal silica (e.g. Aerosil) 0 to 0–5% w/w, preferably 0.25 to 3% w/w, pyrogenic silica 0 to 2% w/w, preferably 0.25 to 1% w/w, hydrated sodium silicoaluminate 0 to 2% w/w, preferably 0.5 to 1% w/w, colloidal silicon dioxide 0 to 0.5% w/w.

g) Flavouring agents: are used in for example approximate quantities of 0 to 5% w/w, preferably 0.25 to 2% w/w, orange, cherry and strawberry, raspberry, grape and passion fruit.

h) Sweetening agents: for example sodium saccharin 0 to 10% w/w, preferably, 0.5 to 5.0% w/w, aspartame 0 to 10% w/w, preferably 0.25 to 5.0% w/w, confectioners sugar 0 to 30% w/w, preferably 5 to 20% w/w, sorbitol 25 to 90% w/w, preferably 0.5 to 10% w/w, sucrose 0 to 85% w/w, preferably 0.5 to 20% w/w, xylitol 0–20% w/w, preferably 0.5 to 10% w/w.

Such materials may be incorporated at the appropriate stage(s) of the manufacturing process together with any other agents (e.g. colourants).

Based on the teachings and principles set out herein, the following generally formulations are illustrative of tablets of the invention, and the skilled man given these teachings and principles will be able to make specific tablet formulations in accordance with the invention.

| INGREDIENT | CONCENTRATION (% w/w) in Tablet |
|---|---|
| Acyclovir | 5 to 90 |
| Swellable clay | 0.25 to 60 (perferably 0.25 to 50) |
| Binder | 0 to 25 |
| Disintegrating agent | 0 to 20 |
| Water-soluble filler | 0 to 95 |
| Water-insoluble filler | 0 to 95 |
| Wetting agent | 0 to 5 |
| Lubricant | 0.1 to 5 |
| Colours, flavours, sweeteners | 0 to 10 |
| Approximate Tablet weight: | 50–2000 mg |

Other aspects of the tablet preparation with now be discussed.

Suitably the dry mixing is effected with a mixing time of 5 minutes to 25 minutes preferably about 10 minutes.

The swellable clay can be dry mixed with acyclovir and other excipients and then granulating solution added, or the clay and other excipients can be dispersed firstly in the granulating solution and then added to the acyclovir and any other excipients prior to granulation.

The liquid employed to moisten the dry mixture, prior to the granulation step, is preferably aqueous, for example water or a mixture of water and a suitable alcohol such as ethanol or isopropanol.

Wet mixing of granulating times which are suitable (depending on the type of mixer used) are 5 to 20 minutes.

Suitable granule drying times and conditions (which will vary according to the type of equipment used and batch size of granules) are about 50° to 80° C., (using a dryer such as with a tray or fluid bed dryer) to obtain a moisture content generally below about 4%.

Generally suitable compression weights and final table hardness will vary according to the size of tablet, but generally suitable values are as follows:

| Approximate Tablet weight (mg) | Approximate Tablet diameter (mm) | Approximate Target tablet hardness (Kp) |
|---|---|---|
| 60 | 5.6 | 1–2 |
| 80 | 6.4 | 3–4 |
| 125 | 7.4 | 4–5 |
| 250 | 8.6 | 5–6 |
| 330 | 9.4 | 6–8 |
| 500 | 11.0 | 10–12 |
| 600 | 11.8 | 10–14 |
| 1000 | 14.0 | 12–16 |

The tablets may optionally be film-coated, for example with hydroxypropylmethyl cellulose, polyethylene glycol or titanium dioxide, and/or may be scored and/or may be polished, for example with polyethylene glycol 8000. If the tablets are film-coated, this makes them easier to swallow or chew (i.e. the tablets are suitable for either dispersion in water or for direct swallowing or chewing), but the dispersion time is increased.

The present invention also provides:

a) Granules containing acyclovir and a pharmaceutically acceptable swellable clay, suitable for use is the preparation of a water-dispersible table according to the invention.

b) Use of granules as defined above in the preparation of a water-dispersible table according to the invention. Optionally, a further amount of swellable clay may be added after granulation and before compression.

c) Use of a pharmaceutically acceptable swellable clay as a dispersing agent in the preparation of a water-dispersible tablet containing acyclovir;

d) Use in human medicinal therapy of a water-dispersible tablet comprising acyclovir, together with an effective amount of pharmaceutically acceptable swellable clay within the granules of the tablet.

Suitably the swellable clay of the invention is a pharmaceutically acceptable crystalline mineral compound, such as aluminum magnesium silicate (e.g. Veegum).

The therapeutic use of a tablet of the invention includes both treatment and prophylaxis.

Yet further aspect of the invention are as follows:

l) A granulate comprising acyclovir together with a pharmaceutically acceptable magnesium aluminum silicate compound;

m) Use of a granulate according to l) above for the manufacture of a water-dispersible tablet formulation.

n) Use of magnesium aluminum silicate in the manufacture of a water-dispersible tablet formulation of acyclovir.

o) A water-dispersible pharmaceutical tablet formulation comprising acyclovir together with a pharmaceutically acceptable magnesium aluminium silicate compound.

p) A process for the preparation of a pharmaceutical tablet formulation which comprises admixing acyclovir with a magnesium aluminum silicate compound and optionally one or more further pharmaceutical carriers or excipients, granulating the resulting mixture with a pharmaceutically acceptable liquid, drying the resulting granulate, optionally mixing the dried granulate with one or more further pharmaceutical carriers or excipients, and subsequently compressing the dried granulate to form tablets. The liquid employed in the above granulation step is advantageously aqueous, for example, an aqueous ethanol mixture. The resulting tablets may be subsequently film coated for example with hydroxypropylmethyl cellulose, titanium dioxide or polyethylene glycol and, if desired, polished for example with polyethylene glycol 8000.

Tablets according to the invention containing acyclovir advantageously include a magnesium aluminium silicate such as Veegum F as the swellable clay optionally together with further pharmaceutical carriers or excipients referred to above such as disintegrating agents, binders, fillers, lubricants etc.

In such tablets the ingredients are advantageously present in the following proportions: acyclovir 40 to 98% w/w, preferably 75 to 85% w/w, swellable clay 0.5 to 40% w/w, preferably 0.5 to 10% w/w.

A suitable formulation of an acyclovir dispersible tablet containing from 200 mg–800 mg acyclovir would be:

| | |
|---|---|
| Acyclovir | 0% w/w to 90% w/w, preferably 75–85% w/w |
| Povidone or pregelled starch | 0.25% w/w to 5% w/w, preferably 0.5–2% w/w |
| Magnesium aluminium silicate Veegum F or bentonite | 0.5% w/w to 30% w/w, preferably 0.5–10% w/w |
| Microcrystalline cellulose Avicel PH101 or LHPC-LH11 | 5% w/w to 25% w/w, preferably 5–15% w/w |
| Sodium starch glycollate | 0% w/w to 8% w/w, preferably 0–5% w/w |
| Magnesium stearate and if optionally film coated: | 0.25% w/w to 2% w/w, preferably 0.25–1.0% w/w |
| Opadry | 0.1% w/w to 2% w/w, preferably 0.25–1.0% w/w |
| Polyethylene glycol 8000 | 0.1% w/w to 0.5% w/w, preferably 0.1–0.2% w/w |

DESCRIPTION OF THE PREFERRED EMBODIMENTS

The following Examples illustrates the present invention. Examples 1 to 6 and 29 are composition examples while example 7–28, 30 and 31 describe the preparation of tablets according to the invention.

| Example Number | 1 mg/tablet | 2 mg/tablet | 3 mg/tablet | 4 mg/tablet |
|---|---|---|---|---|
| Intra-granular: | | | | |
| Acyclovir * | 848.0 | 848.0 | 844.0 | 844.0 |
| Avicel PH101 | 60.0 | NIL | 101 | NIL |
| Lactose | 120.0 | NIL | NIL | NIL |
| Starch (maize) | NIL | NIL | 50 | NIL |
| Explotab | NIL | 75.0 | 50 | NIL |
| Primogel | NIL | NIL | NIL | 75.0 |
| Ac-Di-Sol | 83.0 | NIL | 23 | NIL |
| Kollidon CL starch | NIL | NIL | NIL | NIL |
| Saccharin sodium | 20.0 | 10.0 | NIL | NIL |
| Sodium lauryl sulphate | 5.0 | NIL | 3.0 | NIL |
| Sodium docusate | NIL | 1.0 | NIL | 0.5 |
| Dicalc.phosph.dihyr. | NIL | NIL | NIL | 200.0 |
| Povidone K30 | NIL | 10.0 | 22 | 11.2 |
| Extra-granular: | | | | |
| Ac-Di-Sol | 40.0 | NIL | NIL | NIL |
| Avical PH102 | 60.0 | 94 | NIL | NIL |
| Amberlite IRP88 | NIL | NIL | NIL | 50.0 |
| Kollidon CL | NIL | NIL | 60.1 | NIL |
| Mg stearate | 12.0 | 10.0 | 10.1 | 11.0 |
| Tablet weight (mg) | 1248.0 | 1048.0 | 1163.2 | 1191.7 |

| Example Number | 5 mg/tablet | 6 mg/tablet | 7 mg/tablet | 8 mg/tablet | 9 mg/tablet |
|---|---|---|---|---|---|
| Acyclovir | 844.0 | 848.0 | 844.0 | 848.0 | 848.0 |
| Avicel PH 101 | 101.0 | 83.46 | 100.0 | 89.0 | 89.0 |
| Veegum F | NIL | NIL | 53.0 | 53.0 | 53.0 |
| Sodium starch glycollate (Explotab) | 90.0 | 39.37 | 42.0 | 42.0 | 42.0 |

|  |  |  |  |  |  |
|---|---|---|---|---|---|
| Povidone K30 | 11.0 | 10.27 | NIL | 11.0 | 11.0 |
| Magnesium stearate | 9.5 | 8.85 | 9.4 | 9.4 | 9.4 |
| Film coat composite 1: |  |  |  |  |  |
| Opadry | NIL | NIL | NIL | NIL | 7.86 |
| Film coat composite 2: |  |  |  |  |  |
| Polyethylene glycol 8000 | NIL | NIL | NIL | NIL | 2.097 |
| Tablet weight (mg) | 1055.5 | 989.95 | 1048.4 | 1052.4 | 1062.4 |

*In the following examples except examples 13, 14 and 15, the actual quantity of acyclovir used is calculated from a factor so as to provide 800 mg of acyclovir per tablet. (The factor for acyclovir is typically 105.5 equivalent to 100 acyclovir). In examples 13, 14 and 15, the actual quantity of acyclovir used was adjusted from the factor so as to provide 800 mg of acyclovir per tablet.

In accordance with the invention, to illustrate that the disintegration time remains substantially constant at different tablet hardnesses, the formulation of Example 7 was compressed at approximately 8 kp (7a), 12 kp (7b) and 18 kp (7c) and the results noted hereafter.

| Example Number | 10 mg/tablet | 11 mg/tablet | 12 mg/tablet |
|---|---|---|---|
| Acyclovir | 848.0 | 848.0 | 848.00 |
| Avicel PH 101 | 118.5 | 71.1 | 86.8 |
| Veegum F | 26.5 * | 53.0 | 53.0 |
| Primojel | 42.0 | 42.0 | 42.0 |
| Povidone K30 | NIL | 20.9 | 5.2 |
| Magnesium stearate | 9.4 | 9.4 | 9.4 |
| Tablet weight (mg) | 1044.4 | 1044.4 | 1044.4 |

Examples of Acyclovir formulations

| Example Number | 13 mg/tablet | 14 mg/tablet | 15 mg/tablet |
|---|---|---|---|
| Component (mg/tablet) |  |  |  |
| Acyclovir | 800.0 | 800.0 | 800.0 |
| Avicel PH 101 | 100.0 | 89.0 | 89.0 |
| Veegum F | 53.0 | 53.0 | 110.0 |
| Sodium starch glycollate | 42.0 | 42.0 | 42.0 |
| Povidone K30 | NIL | 11.0 | 11.0 |
| Magnesium stearate | 9.4 | 9.4 | 9.9 |
| Tablet weight (mg) | 1004.4 | 1004.4 | 1061.9 |

| Example Number | 16 % w/w | 16 mg/tablet | 17 % w/w | 17 mg/tablet | 18 % w/w | 18 mg/tablet | 19 % w/w | 19 mg/tablet |
|---|---|---|---|---|---|---|---|---|
| Acyclovir | 79.95 | 848.0 | 75.54 | 795.00 | 65.47 | 689.00 | 55.00 | 583.00 |
| Avicel PH101 | 8.86 | 89.0 | 8.86 | 89.00 | 8.86 | 89.00 | 8.86 | 89.00 |
| Veegum F | 5.28 | 53.0 | 10.00 | 106.00 | 20.00 | 212.00 | 30.00 | 318.00 |
| Explotab | 4.18 | 42.0 | 4.18 | 42.00 | 4.18 | 42.00 | 4.18 | 42.00 |
| Povidone K30 | 1.09 | 11.0 | 1.09 | 11.00 | 1.09 | 11.00 | 1.09 | 11.00 |
| Magnesium stearate | 0.94 | 9.4 | 0.94 | 9.40 | 0.94 | 9.40 | 0.94 | 9.40 |
| Tablet weight (mg) | 100.0 | 1052.4 | 100.0 | 1052.4 | 100.0 | 1052.4 | 100.0 | 1052.4 |

| Example Number | 20 % w/w | 20 mg/tablet | 21 % w/w | 21 mg/tablet | 22 % w/w | 22 mg/tablet |
|---|---|---|---|---|---|---|
| Acyclovir | 45.32 | 477.00 | 84.3 | 890.00 | 44.93 | 848.00 |

-continued

| | | | | | | | |
|---|---|---|---|---|---|---|---|
| Avicel PH101 | 8.86 | 89.00 | 8.86 | 89.00 | 8.86 | 157.76 | |
| Veegum F | 40.00 | 424.00 | 1.00 | 10.60 | 40.00 | 712.22 | |
| Explotab | 4.18 | 42.00 | 4.18 | 42.00 | 4.18 | 74.43 | |
| Povidone K30 | 1.09 | 11.00 | 1.09 | 11.00 | 1.09 | 19.41 | |
| Magnesium stearate | 0.94 | 9.40 | 0.94 | 9.40 | 0.94 | 16.74 | |
| Tablet weight (mg) | 100.00 | 1052.4 | 100.00 | 1052.4 | 100.00 | 1828.56 | |

| Example Number | 23 | | 24 | | 25 | | 26 | |
|---|---|---|---|---|---|---|---|---|
| | % w/w | mg/tablet | % w/w | mg/tablet | % w/w | mg/tablet | % w/w | mg/tablet |
| Acyclovir | 65.47 | 689.00 | 55.00 | 583.00 | 45.32 | 477.00 | 79.65 | 848.00 |
| Avicel PH101 | 8.86 | 89.00 | 8.86 | 89.00 | 8.86 | 89.00 | 8.86 | 89.0 |
| Veegum F | *20.00 | (106.00 (106.00 | *30.00 | (159.00 (159.00 | *40.00 | (212.00 (212.00 | 5.28 | 53.0 |
| Explotab | 4.18 | 42.00 | 4.18 | 42.00 | 4.18 | 42.00 | 4.18 | 42.0 |
| Povidone K30 | 1.09 | 11.00 | 1.09 | 11.00 | 1.09 | 11.00 | 1.09 | 11.0 |
| Magnesium stearate | 0.94 | 9.40 | 0.94 | 9.40 | 0.94 | 9.40 | 0.94 | 9.4 |
| Tablet weight (mg) | 100.00 | 1052.4 | 100.00 | 1052.4 | 100.00 | 1052.4 | 100.00 | 1052.4 |

| Example Number | 27 | | 28 | | 29 | | 30 | 31 |
|---|---|---|---|---|---|---|---|---|
| | % w/w | mg/tablet | % w/w | mg/tablet | % w/w | mg/tablet | mg/tablet | mg/tablet |
| Acyclovir | 84.43 | 848.00 | 84.68 | 848.00 | 84.93 | 848.00 | 848.0 | 840.0 |
| Avicel PH101 | 8.86 | 83.95 | 8.86 | 83.70 | 8.86 | 83.46 | 89.0 | 89.0 |
| Veegum F | 0.50 | 4.74 | 0.25 | 2.36 | 0.00 | 0.00 | — | - |
| Bentonite | — | — | — | — | — | — | 53.0 | NIL |
| Attapulgite | — | — | — | — | — | — | NIL | 53.0 |
| Explotab | 4.18 | 39.60 | 4.18 | 39.49 | 4.18 | 39.37 | 42.0 | 42.0 |
| Povidone K30 | 1.09 | 10.32 | 1.09 | 10.30 | 1.09 | 10.27 | 11.0 | 11.0 |
| Magnesium stearate | 0.94 | 8.91 | 0.94 | 8.88 | 0.94 | 8.85 | 9.1 | 9.1 |
| Tablet weight (mg) | 100.00 | 995.53 | 100.00 | 992.73 | 100.00 | 989.95 | 1052.1 | 1044.1 |

* Veegum added as a paste - example contains no PVP-K30 as a binder.
* In these examples the Veegum is distributed equally both intra-granularly and extra-granularly.

Method of Preparation

The tablets described in Examples 1–31 above were prepared according to the following general method:

(a) A dry mixture was made of all components except Povidone/PVP K30, sodium docusate (if present) and magnesium stearate;

(b) The Povidone/PVP K30 and sodium docusate (if present) were dissolved in 50% aqueous alcohol to form a granulation solution;

(c) The granulation solution was added to the dry mixture to form granules;

(d) The wet granules were dried in a fluid bed dryer;

(e) The granules were then sifted through a 1000 μm diameter mesh sieve; and (f) The dried granules were blended with the magnesium stearate and compressed to form tablets.

Flavouring agents where present were added at blending step (f) above.

This general method is illustrated with respect to the following specific examples.

EXAMPLE 8

Uncoated Tablets (a) A dry mixture was made of all components except Povidone/PVP K30 and magnesium stearate using a Diosna P100 (high shear mixer-granulator) for 3 minutes.

(b) The Povidone/PVP K30 was dissolved in 50% aqueous alcohol to form a granulation solution.

(c) The granulation solution was added to an approximate quantity of 300 ml per kg dry weight to the dry mixture to form granules. Wet mixing was carried out for approximately 5 minutes.

(d) The wet granules were dried in an Aeromatic T3 fluid bed drier at a temperature of 70° C. for approximately 30 minutes. The moisture content of the granules was approximately 4%.

(e) The granules were then sifted through a 1000 μm diameter mesh sieve using a Jackson Crockatt No. 7 sifter.

(f) The dried granules were blended with the magnesium stearate using a collette mixer for approximately 10 minutes and compressed to form tablets using a Manesty D3 Rotary tablet press fitted with caplet shaped punches of approximately 19.3 mm length and 9.0 mm breadth. Tablets were compressed to a weight of 1052 mg±2%.

This granule can be used to make other strengths of acyclovir dispersible tablets, e.g. 200 mg and 400 mg, compressing the dried granules to a weight of respectively 263 mg and 526 mg, using round punches with diameters of respectively 11.0 mm and 8.6 mm.

EXAMPLE 9

Film Coated Tablets

Steps (a) to (f) described in Example 8 were repeated to form an uncoated tablet which was then film-coated by the following procedure.

The film-coating apparatus used was a Manesty Accellacota 10. The coating suspension was sprayed onto the tablet cores to a target weight increase of between 0.5–1.0% using suitable parameters of:

pan rotation speed (8.5 rpm)

spray (application rate (~20 g per min)

inlet temperature (~75° C.)

exhaust temperature (~53° C.).

A polish coat of PEG8000 was then applied to the film-coated tablets, to a further weight gain of 0.1–0.2%.

EXAMPLES 13 TO 15

In Example 13, Acyclovir, Avicel PH101, Sodium starch glycollate and Veegum F are dry mixed in a mixer. The mixture is then granulated after adding a sufficient volume of 50% aqueous alcohol (IMS). The resulting granules are dried, blended with the magnesium stearate and then compressed to form tablets.

EXAMPLE 14

The procedure described in Example 13 for the preparation of the granules and formation of the tablets is employed except that granulation of the dry mixture is effected with the Povidone in a 50% aqueous alcohol solution. Film coating of the resulting tablets can be optionally effected by treating the tablets with a dispersion of Opadry white dispersion in purified water and drying the coated tablets which are subsequently polished with a solution of polyethylene glycol 8000, USNF in 50% aqueous alcohol (IMS).

For Example 15, the procedure described in Example 13 for the preparation of the granules and formation of the tablets is employed except that granulation of the dry mixture was effected with the Povidone in a 50% aqueous alcohol solution.

The tablets prepared in accordance with the above Examples were then tested as follows.

Tablet Evaluation Methods

1. Average tablet weight. Twenty tablets were weighed on an analytical balance and the average tablet weight calculated.

2. Tablet breaking strength (kilo bond-kp). 5 tablets were individually tested using a Schleuniger crushing strength tester, and the average breaking strength calculated.

3. Friability (% loss). 10 tablets, accurately weighed, were subjected to 10 minutes friability testing using a Roche Friabilator. The tablets were dedusted, reweighed, and the weight loss due to the friability was calculated as a percentage of the initial weight.

4. Dispersion Disintegration time DT (BP 1988). 6 tablets were tested in accordance to the above-defined BP test (without discs) for dispersible tablets. This utilises water at a temperature of 19°–21° C.

5. Dispersion Quality. In accordance with the BP uniformity of dispersion test for dispersible tablets (BP 1988 Volume II page 895), two tablets were placed in 100 ml of water at 19°–21° C. and allowed to disperse. A smooth dispersion was produced which passed through a 710 µm mesh sieve.

Granule Evaluation Methods

1. Loss on Drying (LOD). The residual moisture content of the granule (LOD) was determined on a 3–4 g sample using a Computrac moisture analyser set at 90° C. operated in accordance with the manufacturer's procedure.

2. Weight Median Diameter (WMD). A 10 g sample of granule was sifted for 2 minutes at suitable pulse and sift amplitudes in an Allen Bradley sonic sifter in accordance with manufacturer's instructions. Sieves of 710 µm, 500 µm, 355 µm, 250 µm, 150 µm, 106 µm and 53 µm were used. The WMD was calculated from the cumulative percentage undersize size distribution using a computer programme.

Acyclovir Granule and Tablet Evaluation Results

| Example Number | Actual Average Tablet Weight (mg) | Target Tablet Weight (mg) | Average Thickness (mm) | Average Breaking Strength (Kp) | Friability (%) | Disintegration time ** First Tablet | Disintegration time ** Last Tablet | Loss on Drying (% LOD) | Granule Properties WMD (µm) Weight median diameter | Tablet shape/ maximum diameter |
|---|---|---|---|---|---|---|---|---|---|---|
| 1 | — | 1248.0 | — | 11.0 | — | | 12'17" | 1.43 | — | Caplet* |
| 2 | — | 1048.0 | — | 11.6 | — | | 7'26" | 1.59 | — | Caplet |
| 3 | 1176 | 1163.2 | — | 10.7 | — | >10' | >10' | 2.28 | — | Round 14.0 mm |
| 4 | — | 1191.7 | — | 13.7 | | | 4'50" | 1.18 | — | Round 14.0 mm |
| 5 | 1053 | 1055.5 | — | 15.0 | — | | 4'21" | 1.75 | 186 | Round 14.0 mm |
| 6 | 983 | 989.95 | 5.46 | 10.8 | 0.34 | 6'27" | 7'26" | 1.43 | 315 | Caplet |
| 7a | 1022 | 1048.4 | — | 7.2 | 2.74 | | 0'33" | 1.31 | 233 | Caplet |
| 7b | 1046 | 1048.4 | — | 12.8 | 0.47 | | 0'42" | 1.31 | 233 | Caplet |
| 7c | 1048 | 1048.4 | — | 17.1 | 0.19 | | 0'44" | 1.31 | 233 | Caplet |
| 8 (uncoated) | 1049 | 1052.4 | 7.0 | 14.6 | 0.18 | | 0'35" | 4.06 | 138 | Caplet |
| 9 (coated) | 1053 | 1062.4 | 6.99 | 16.1 | negligible | | 1'05" | 4.06 | 138 | Caplet |

-continued

Acyclovir Granule and Tablet Evaluation Results

| Example Number | Actual Average Tablet Weight (mg) | Target Tablet Weight (mg) | Average Thickness (mm) | Average Breaking Strength (Kp) | Friability (%) | Disintegration time** First Tablet | Disintegration time** Last Tablet | Granule Properties Loss on Drying (% LOD) | Weight median WMD (μm) | Tablet shape/ maximum diameter |
|---|---|---|---|---|---|---|---|---|---|---|
| 10 | — | 1044.4 | — | 14.4 | 0.11 | — | 0'32" | 2.65 | 123 | Caplet |
| 11 | — | 1044.4 | — | 15.3 | 0.24 | — | 0'46" | 1.46 | 196 | Caplet |
| 12 | — | 1044.4 | — | 13.3 | 0.73 | — | 0'27" | 1.76 | 105 | Caplet |
| 13, 14, 15*** | | | | | | | | | | |
| 16 | 1051.24 | 1052.4 | 7.1 | 11.6 | 0.49 | 0'46" | 0'49" | 1.12 | 185 | Caplet |
| 17 | 1059.54 | 1052.4 | 7.0 | 11.8 | 0.46 | 0'28" | 0'30" | 2.18 | 125 | Caplet |
| 18 | 1060.79 | 1052.4 | 6.90 | 11.5 | 0.62 | 0'17" | 0'19" | 1.46 | 178 | Caplet |
| 19 | 1053.4 | 1052.4 | 6.70 | 11.6 | 0.71 | 0'19" | 0'24" | 2.00 | 73 | Caplet |
| 20 | 1057.6 | 1052.4 | 6.71 | 9.1 | 2.45 | 0'20" | 0'23" | 1.81 | 90 | Caplet |
| 21 | 1048.8 | 1052.4 | 7.24 | 11.5 | 0.85 | 2'18" | 2'59" | 1.15 | 341 | Caplet |
| 22 | 1743.9 | 1828.56 | 10.40 | 11.6 | 2.19 | 0'29" | 0'31" | 1.84 | 83 | Caplet |
| 23 | 1054.2 | 1052.4 | 6.90 | 11.5 | 0.09 | 0'43" | 0'51" | 1.84 | 157 | Caplet |
| 24 | 1059.1 | 1052.4 | 6.90 | 11.4 | 0.02 | 0'55" | 1'00" | 0.68 | 142 | Caplet |
| 25 | 1052.6 | 1052.4 | 6.70 | 11.9 | 0.09 | 1'30" | 1'42" | 1.59 | 118 | Caplet |
| 26a)# | 130.6 | 131.55 | 2.80 | 4.2 | 0.56 | 0'25" | 0'28" | 1.34 | 296 | 7.4 mm Round |
| 26b)# | 526.0 | 526.2 | 4.81 | 12.84 | 0.79 | 0'26" | 0'30" | 1.34 | 296 | 11.0 mm Round |
| 26c)# | 1216.5 | 1215.0 | 8.20 | 11.10 | 0.83 | 0'45" | 0'51" | 1.34 | 296 | Caplet |
| 27 | 125.7 | 124.4 | 3.69 | 3.69 | 0.71 | 0'33" | 0'39" | 1.21 | 334 | 7.4 mm Round |
| 28 | 124.7 | 124.1 | 2.78 | 3.55 | 0.65 | 0'44" | 0'47" | 1.90 | 332 | 7.4 mm Round |
| 29 | 982.9 | 989.95 | 5.46 | 10.8 | 0.34 | 6'27" | 7'26" | 1.43 | 315 | Caplet |
| 30 | 1041.2 | 1052.1 | — | 11.8 | — | 1'30" | 1'55" | 1.62 | 227 | Caplet |
| 31 | 1038.6 | 1044.1 | — | 16.6 | 1.59 | 1'50" | 2'10" | 1.96 | 150 | Caplet |

**All dispersions passed through a 710 m sieve (BP uniformity od dispersion test)
*Approximate dimensions of caplet were: 19.3 mm long, 9.0 mm wide, 7.0 mm thick.
**Disintegration times measured in accordance with BP test for dispersible tablets. All dispersions passed through a 710 m sieve (BP uniformity of dispersion) and c = 925 mg of acyclovir per tablet.
Same granule formulation, but different compression weights giving approximately: a = 100 mg, b = 400 mg and c = 925 mg of acyclovir per tablet.
***Examples 13, 14 and 15 disintegrated in 0'30" to 1'30".

A particle size analysis was carried out on the dispersion of a tablet of Example 9 in accordance with the following method.

The particle size distribution was determined using a Malvern 2600 particle analyser as follows. The instrument was set to analyse particles in liquid with magnetic stirrer fitted. A 300 mm focal length lens was used.

1. Dispersion tablet in 100 ml of de-ionised water.
2. Agitate solution for approximately 2 hours.
3. Filter or centrifuge solution to obtain liquor which should be saturated with all ingredients present in the tablet.
4. Disperse second tablet in 50 ml of saturated liquor allowing 3 minutes to fully disperse. Agitate vigorously and remove a sample of the dispersion within 5 minutes adding sufficient quantity to the Malvern PLL cell containing the liquor to obtain an observation value of 0.15–0.30. Analyse sample.

The particle size distribution was as follows:
Particle size: (as equivalent spherical volume)
<710 μm–100%
<300 μm–98.7%
<200 μm–86.7%
<130 μm–50% (median particle size).

I claim:

1. A water-dispersible tablet composed of granules having 200 to 800 mg of acyclovir, said tablet consisting essentially of:

within said granules, 20 to 90% w/w acyclovir, 0 to 25% w/w binder, 0.25 to 60% w/w of a non talc swellable clay, and a disintegrating agent; and outside the granules, lubricant; to provide a dispersion which is capable:

a) of dispersing in water to provide a dispersion which passes through a sieve screen with a mesh aperture of 710 μm; and b) of disintegrating within three minutes when examined by the following apparatus and method in accordance with the test for dispersible tablets of the British Pharmacopoeia, 1988, volume II, page 895; said apparatus consisting of:

(i) a rigid basket-rack assembly supporting six cylindrical glass tubes 75.0 to 80.0 mm long, 21.5 mm in internal diameter and with a wall thickness of about 2 mm;

(ii) a cylindrical disc for each tube, each 20.55 to 20.85 mm in diameter and 9.35 to 9.65 mm thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disc in such a way that at the upper surface of the disc they are 9.5 mm wide and 2.55 mm deep and at the lower surface 1.6 mm square;

(iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate;

(iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 nd 32 cycles per minute;

(v) said assembly being suspended in water at 19° to 21° C. held in a 1000 ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water;

said method consisting of introducing one tablet into each of the six tubes, suspending said assembly in the beaker containing the water and operating the apparatus for a maximum period of three minutes so that all six of the tablets disperse.

2. A tablet as claimed in claim 1, wherein the swellable clay is a smectite or attapulgite.

3. A tablet as claimed in claim 2, wherein the smectite is a montmorilanoid.

4. A tablet as claimed in claim 3, wherein the montmorilanoid is magnesium aluminum silicate or bentonite.

5. A tablet as claimed in claim 1, 2, 3 or 4, wherein the swellable clay is present within the granules of the tablet in an amount of 1 to 10% w/w.

6. A tablet as claimed in claim 1, wherein the disintegrating agent is sodium starch glycolate or lowhydroxypropylcellulose.

7. A tablet as claimed in claim 1, wherein the binder is povidone.

8. A tablet as claimed in claim 1, 2, 3, 4, 5 or 6 which further comprises a filler.

9. A tablet as claimed in claim 8, wherein the filler is microcrystalline cellulose.

10. A tablet as claimed in claim 1, which is further film coated and wherein the dispersion time can be up to 5 minutes.

11. A tablet as claimed in claim 1, which is capable of dispersing in water within a period of 2 minutes.

12. A tablet as claimed in claim 1, wherein the dispersion contains particles having a particle size distribution of 100% less than 710 μm, and more than 50% less than 300 μm.

13. A tablet as claimed in claim 12, wherein the dispersion contains particles having a particle size distribution of 100% less than 710 μm, more than 70% less than 300 μm, and more than 50% less than 200 μm.

14. A tablet as claimed in claim 1, wherein the acyclovir is present in an amount from 750 to 850 mg, the total weight is 1000 to 1200 mg, and the amount of swellable clay present in an amount from 40 to 120 mg.

15. A water-dispersible tablet composed of granules having 200 to 800 mg of acyclovir, said tablet consisting essentially of:

within said granules, 20 to 90% w/w acyclovir, 0 to 25% w/w binder, 0.25 to 60% w/w of a non talc swellable clay selected from the group consisting of smectite and attapulgite, and up to 10% w/w sodium starch glycolate or an effective amount of lowhydroxypropylcellulose; and outside the granules, lubricant;

to provide a tablet which is capable:

a) of dispersing in water to provide a dispersion which passes through a sieve screen with a mesh aperture of 710 μm; and b) of disintegrating within three minutes when examined by the following apparatus and method in accordance with the test for dispersible tablets of the British Pharmacopoeia, 1988, volume II, page 895; said apparatus consisting of:

(i) a rigid basket-rack assembly supporting six cylindrical glass tubes 75.0 to 80.0 mm long, 21.5 mm in internal diameter and with a wall thickness of about 2 mm;

(ii) a cylindrical disc for each tube, each 20.55 to 20.85 mm in diameter and 9.35 to 9.65 mm thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disc in such a way that at the upper surface of the disc they are 9.5 mm wide and 2.55 mm deep and at the lower surface 1.6 mm square;

(iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate;

(iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 nd 32 cycles per minute;

(v) said assembly being suspended in water at 19° to 21° C. held in a 1000 ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water;

said method consisting of introducing one tablet into each of the six tubes, suspending said assembly in the beaker containing the water and operating the apparatus for a maximum period of three minutes so that all six of the tablets disperse.

16. A water dispersible tablet composed of granules having 200 mg to 800 mg of acyclovir, said tablet consisting essentially of:

within said granules, 70 to 90% w/w acyclovir, 0.25 to 5% w/w povidone or pregelled starch, 0.5 to 30% w/w magnesium aluminum silicate or bentonite, 5 to 25% w/w microcrystalline cellulose or lowhydroxypropylcellulose, and 0 to 8% w/w sodium starch glycolate; and outside the granules, 0.25 to 2% w/w magnesium stearate and optional film-coating composites of opadry 0.1 to 2% w/w, and polyethylene glycol 0.1 to 0.5 w/w;

to provide a tablet which is capable:
  a) of dispersing in water to provide a dispersion which passes through a sieve screen with a mesh aperture of 710 μm; and
  b) of disintegrating within three minutes when examined by the following apparatus and method in accordance with the test for dispersible tablets of the British Pharmacopoeia, 1988, volume II, page 895; said apparatus consisting of:
    (i) a rigid basket-rack assembly supporting six cylindrical glass tubes 75.0 to 80.0 mm long, 21.5 mm in internal diameter and with a wall thickness of about 2 mm;
    (ii) a cylindrical disc for each tube, each 20.55 to 20.85 mm in diameter and 9.35 to 9.65 mm thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disc in such a way that at the upper surface of the disc they are 9.5 mm wide and 2.55 mm deep and at the lower surface 1.6 mm square;
    (iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate;
    (iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 nd 32 cycles per minute;
    (v) said assembly being suspended in water at 19° to 21° C. held in a 1000 ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water;

said method consisting of introducing one tablet into each of the six tubes, suspending said assembly in the beaker containing the water and operating the apparatus for a maximum period of three minutes so that all six of the tablets disperse.

17. A tablet as claimed in claim 16, wherein the formulation is acyclovir 75 to 85% w/w, povidone or pregelled starch 0.5 to 2% w/w, magnesium aluminum silicate or bentonite 0.5 to 10% w/w, microcrystalline cellulose or lowhydroxypropylcellulose 5 to 15% w/w, sodium starch glycolate 0 to 5% w/w, magnesium stearate 0.25 to 1.0 w/w, and optional film-coating composites of opadry 0.25 to 1.0% w/w, and polyethylene glycol 0.1 to 0.2% w/w.

18. A tablet as claimed in claim 1 or claim 16, containing 400 to 800 mg acyclovir.

19. A tablet as claimed in claim 1 or claim 16, wherein the disintegrating agent is selected from the group consisting of microcrystalline cellulose, sodium carboxymethyl cellulose, calcium carboxymethyl cellulose, modified cellulose gum, cross-linked povidone, alginic acid, alginates, pregelatinized starch, sodium starch glycolate, modified corn starch, starch and polacrin potassium.

20. A process for the preparation of water dispersible tablet having 200 to 800 mg of acyclovir, the process consisting essentially of the steps:
  a) admixing dry: at least 60% w/w acyclovir, 0.25 to 40% w/w of a swellable clay, and a disintegrating agent;
  b) adding 0 to 25% w/w binder, in solution, to moisten the dry mixture;
  c) granulating of the resulting moist mixture to form granules;
  d) drying the granules and blending the granules with lubricant;
  e) compressing of the granules to form a tablet;
  f) the tablet dispersing in water to provide a dispersion which passes through a sieve screen with a mesh aperture of 710 μm;
  g) the tablet disintegrating within three minutes when examined by the following apparatus and method in accordance with the test for dispersible tablets of the British Pharmacopoeia, 1988, volume II, page 895; said apparatus consisting of:
    (i) a rigid basket-rack assembly supporting six cylindrical glass tubes 75.0 to 80.0 mm long, 21.5 mm in internal diameter and with a wall thickness of about 2 mm;
    (ii) a cylindrical disc for each tube, each 20.55 to 20.85 mm in diameter and 9.35 to 9.65 mm thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disc in such a way that at the upper surface of the disc they are 9.5 mm wide and 2.55 mm deep and at the lower surface 1.6 mm square;
    (iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate;
    (iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 nd 32 cycles per minute;
    (v) said assembly being suspended in water at 19° to 21° C. held in a 1000 ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water;

said method consisting of introducing one tablet into each of the six tubes, suspending said assembly in the beaker containing the water and operating the apparatus for a maximum period of three minutes so that all six of the tablets disperse.

21. A method for the treatment of a herpes viral infection, the method consisting essentially of dissolving in water a water-dispersible tablet of acyclovir as defined in claim 1 and, thereafter, drinking the dispersed tablet solution.

* * * * *